(12) United States Patent
Janik et al.

(10) Patent No.: US 6,771,735 B2
(45) Date of Patent: Aug. 3, 2004

(54) METHOD AND APPARATUS FOR IMPROVED X-RAY REFLECTION MEASUREMENT

(75) Inventors: Gary Janik, Palo Alto, CA (US); Jeffrey Moore, Redwood City, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 10/005,610

(22) Filed: Nov. 7, 2001

(65) Prior Publication Data

US 2003/0086533 A1 May 8, 2003

(51) Int. Cl.[7] .............................................. G01N 23/20
(52) U.S. Cl. ....................................................... 378/70
(58) Field of Search ............................. 378/70, 89, 82

(56) References Cited

U.S. PATENT DOCUMENTS

| 4,748,650 | A | 5/1988 | Ammann |
| 5,619,548 | A | 4/1997 | Koppel |
| 5,923,720 | A | 7/1999 | Barton et al. |
| 6,226,349 | B1 | * 5/2001 | Schuster ..................... 378/84 |
| 6,512,814 | B2 | * 1/2003 | Yokhin et al. ................ 378/82 |
| 2002/0097837 | A1 | 7/2002 | Fanton et al. |

OTHER PUBLICATIONS

Publication entitled: "Growth Monitoring of W/Si X-ray Multilayers By X-ray Reflectivity And Kinetic Ellipsometry", Luken et al., SPIE vol. 2253, pp. 327-332.

* cited by examiner

Primary Examiner—Craig E. Church
(74) Attorney, Agent, or Firm—Bever, Hoffman & Harms, LLP; Jeanette S. Harms; John M. Kubodera

(57) ABSTRACT

Thin film thickness measurement accuracy in x-ray reflectometry systems can be enhanced by minimizing scattering and beam spreading effects. An oblong x-ray beam can be produced by shaping the electron beam in an x-ray microfocus tube, or by creating a target with a metal strip having the desired beam cross section. The elongation allows the beam direction dimension to be substantially reduced, without causing overheating of the target. By blocking portions of the x-ray beam focused on the thin film and generating reflectivity curves in increments, the effects of scattering can be minimized.

31 Claims, 14 Drawing Sheets

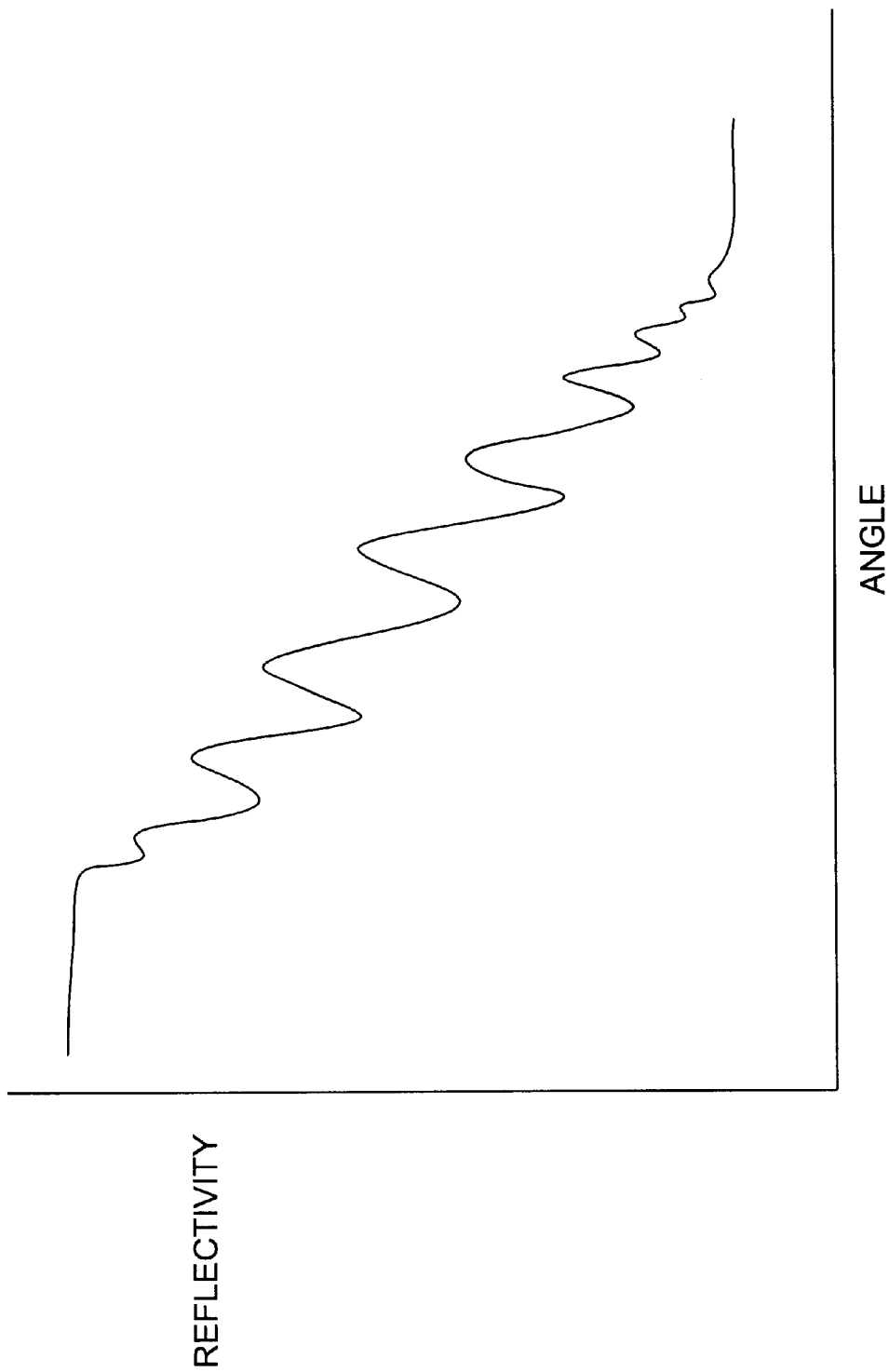

METHOD AND APPARATUS FOR IMPROVED X-RAY REFLECTION MEASUREMENT

BACKGROUND OF THE INVENTION

1. Field of the Invention

The present invention relates to the area of nondestructive film thickness measurement. In particular, the present invention relates to a method and apparatus for improving the resolution and accuracy of x-ray reflectometry measurements of thin films.

2. Discussion of Related Art

Conventional thin film thickness measurement systems often use a technique known as x-ray reflectometry (XRR), which measures the interference patterns created by reflection of x-rays off a thin film. FIG. 1a shows a conventional x-ray reflectometry system 100, as described in U.S. Pat. No. 5,619,548, issued Apr. 8, 1997 to Koppel. X-ray reflectometry system 100 comprises a microfocus x-ray tube 110, an x-ray reflector 120, a detector 130, and a stage 140. A test sample 142 having a thin film layer 141 is held in place by stage 140 for the measurement process.

To measure the thickness of thin film layer 141, microfocus x-ray tube 110 directs a source x-ray beam 150 at x-ray reflector 120. Source x-ray beam 150 actually comprises a bundle of diverging x-rays, including x-rays 151, 152, and 153. X-ray reflector 120 reflects and focuses the diverging x-rays of x-ray beam 150 into a converging x-ray beam 160. Converging x-ray beam 160 includes x-rays 161, 162, and 163, which correspond to x-rays 151, 152, and 153, respectively. Typically, x-ray reflector 120 is a monochromator that ensures that only x-rays of a particular wavelength are included in converging x-ray beam 160.

Converging x-ray beam 160 is then reflected by thin film layer 141 as an output x-ray beam 170 onto detector 130. A detail view of this reflection is shown in FIG. 1b, with reflected x-rays 171, 172, and 173 corresponding to incident x-rays 161, 162, and 163, respectively. The x-rays undergo specular reflection, forcing angles A1, A2, and A3, of x-rays 161, 162, and 163, respectively, to be equal to angles A11, A22, and A33 of x-rays 171, 172, and 173, respectively.

As shown in FIG. 1c, the reflected x-rays are actually formed by reflections at both thin film surface 141a and thin film/substrate interface 142a. Using x-ray 162 as an example, the incident x-ray splits into a primary ray 172a and a secondary ray 172b at thin film layer 141. Primary ray 172a is reflected by thin film surface 141a at an angle A22. Secondary ray 172b is transmitted through thin film layer 141 and is reflected at thin film/substrate interface 142a, eventually exiting thin film surface 141a at angle A22.

Because both rays 172a and 172b exit thin film surface 141a at angle A22, the intensity of x-ray 172 is determined by the amount of constructive or destructive interference between the two rays. The two rays will be in phase if the difference between the optical path length of primary ray 172a and the optical path length of secondary ray 172b is equal to an integer multiple of the wavelength of x-ray 162. (Note that the optical path length of ray 172b includes the distance secondary ray 172b travels within thin film layer 141 multiplied by the index of refraction of thin film layer 141.) If rays 172a and 172b are in phase, the maximum intensity for x-ray 172 is achieved. However, if this optical path length difference is not an integer multiple of the wavelength of x-ray 162, then the two rays will be out of phase, thereby reducing the intensity of x-ray 172.

Note that the actual optical path length of secondary ray 172b within thin film layer 141 is controlled by the incident angle of x-ray 162. Therefore, the intensity of x-ray 172 is ultimately determined by incident angle A2. By simultaneously focusing a beam of x-rays spanning a range of incident angles at the thin film layer, a reflected beam of x-rays having varying intensities can be generated. Those varying intensities can be measured by sensor 130, as indicated in FIG. 1b. For example, reflected x-rays 171, 172, and 173 are shown impinging on a detector plane 130a of detector 130 at points 181, 182, and 183, respectively. Points 181, 182, and 183 typically comprise sensor pixels capable of measuring incident x-ray intensity. The known pixel positions allow detector 130 to correlate the intensities at points 181, 182, and 183 with incident angles A1, A2, and A3, respectively. By performing a similar correlation for all the pixels on detector surface 130a, a reflectivity curve can be derived for thin film layer 140. An example reflectivity curve is shown in FIG. 2. By measuring the fringes in the reflectivity curve, the thickness of thin film layer 140 can be determined, as described in U.S. Pat. No. 5,619,548.

However, accuracy of conventional x-ray reflectometry systems can be severely limited by problems associated with x-ray scattering and spreading at the thin film surface. For example, FIG. 3 shows a detail view of x-ray reflectometry system 100, with incident x-rays 164 and 165 being reflected by thin film layer 141. X-ray 164 has an incident angle A4 and is reflected at an angle A44 as x-ray 174. In accordance with the law of specular reflection, angle A4 is equal to angle A44. X-ray 165 has an incident angle A5, and theoretically would be reflected at an angle A55 as x-ray 175r, where angle A55 is equal to angle A5. Because angle A4 is different from angle A5, x-rays 174 and 175r would ideally impinge on detector surface 130a at points 184 and 185, respectively. However, scattering caused by imperfections in the surface of thin film layer 141 can result in a portion or all of incident x-ray 165 splitting off as x-ray 175s. X-ray 175s leaves the surface of thin film layer 141 at an angle A5s (which is not equal to incident angle A5). If angle A5s happens to be equal to angle A44, both x-rays 175s and 174 will impinge on detector surface 130a at point 184, thereby corrupting the intensity measurements at both points 184 and 185. Scattering is most likely to occur for x-rays having incident angles near the "critical angle" where total external reflection takes place.

The accuracy of conventional x-ray reflectometry systems is further degraded by problems associated with x-ray beam spreading. For example, FIG. 4a depicts the interface between x-ray beam 160 and thin film layer 141 where an illuminated spot B is formed on thin film surface 141a. Compared to a cross section A at the most tightly focused portion of x-ray beam 160, illuminated spot B is significantly elongated in the beam direction. FIG. 4b shows cross section A of x-ray beam 160 overlaid onto illuminated spot B. Conventional microfocus x-ray tubes produce a circular x-ray beam, as indicated in FIG. 4b. Accordingly, the height H1 and width W1 of cross section A are the same (i.e., unitary aspect ratio). In contrast, illuminated spot B is significantly distorted as it spreads across thin film surface 141a, and so has a length L2 and a width W2 at its largest dimensions. In a direction perpendicular to the beam direction and parallel to thin film surface 141a (sometimes referred to as the "neutral axis"), width W2 of illuminated spot B is increased slightly from width W1 of beam cross section A. However, along the beam direction, height H1 of beam cross section A is translated into a significantly greater length L2 of illuminated spot B. This disparity in x-ray beam height and illuminated spot length increases as the incident angle of the incoming x-ray beam decreases, and so is particularly problematic for the grazing-angle x-ray beams required in x-ray reflectometry. For example, at an incident angle of 0.5 degree, the length of the illuminated spot is roughly 100 times greater than the diameter of the x-ray beam.

Because of this lengthening of the illuminated spot, the resolution of conventional x-ray reflectometry systems can be degraded in two main ways. First, the increased illuminated spot size increases the chances that irregularities in the surface of the thin film will lead to scattering of the incident x-rays. Second, the larger spot size can allow reflections of x-rays having different incident angles to impinge on the same point on the detector. For example, if an x-ray reflects from the thin film layer at a point farther from the detector surface than an x-ray having a larger angle of incidence, both reflected x-rays could converge at the same pixel on the detector surface, thereby improperly skewing the measured results. This "overlapping" reflection becomes progressively more prevalent as the spreading of the illuminated spot increases, and can ultimately prevent any measurement of the thin film layer thickness. Note that the increase in illuminated spot width does not present a problem since the key reflection and intensity measurements are all along the beam direction.

Accordingly, it is desirable to provide an x-ray reflectometry system that provides a small illuminated spot size while minimizing the effects of scattering.

SUMMARY

Accordingly, the present invention provides a system and method for enabling high-resolution x-ray reflectometry measurements by minimizing x-ray beam spreading and scattering effects. As noted previously, it is desirable to reduce the size of the x-ray beam used in x-ray reflectometry systems to minimize the effects of beam spreading at the thin film surface. However, reducing the x-ray beam diameter in conventional x-ray microfocus tubes can be difficult. X-rays are produced by aiming a high-energy electron beam (e-beam) at a metal target. This electron bombardment causes the target atoms to emit x-rays, but also significantly heats the exposed portion of the target. Since the energy level of the electrons in the e-beam must remain at a specific level to cause the target atoms to emit the desired x-rays, reducing the cross sectional area of the e-beam increases the energy flux at the exposed portion (source spot) of the target. This in turn increases the required rate of heat conduction away from the source spot to prevent overheating. Therefore, the size of the e-beam is constrained by the thermal conductivity of the target material surrounding the perimeter of the source spot.

An embodiment of the present invention avoids these problems by generating an oblong x-ray beam, rather than the circular x-ray beam generated by conventional microfocus x-ray tubes. By aligning the long dimension of the x-ray beam with the neutral axis in an x-ray reflectometry system, the illuminated spot size can be reduced in the critical beam direction. At the same time, the heat generated by an oblong electron beam in a microfocus x-ray tube can be more efficiently dissipated by the target metal because of the high perimeter to area ratio of such geometries. Therefore, while some benefit over conventional circular x-ray beams will be provided by any beam cross section having a non-unitary aspect ratio (unequal width and height dimensions), a long, narrow beam will typically afford the greatest benefit, by providing a significantly reduced beam dimension coupled with efficient heat dissipation.

For example, a microfocus x-ray tube in accordance with an embodiment of the present invention could generate an x-ray beam from a source spot having a short dimension of roughly 20 $\mu$m and a long dimension of roughly 100 $\mu$m. This would provide substantially the same e-beam cross sectional area as the 50 $\mu$m diameter round source spots commonly used in conventional microfocus x-ray tubes, but with significantly improved heat dissipation and illuminated spot spreading characteristics. In fact, this improved heat dissipation capability provided by the elongated source spot would enable a higher energy density (smaller cross sectional area) e-beam to be used, further reducing the size of the illuminated spot in the critical beam direction.

According to an embodiment of the present invention, a microfocus x-ray tube includes an e-beam shaping element between an electron source and a target. The e-beam shaping element blocks the e-beam produced by the electron source except for a portion of the e-beam having the desired oblong cross section. Electron focusing optics can be included to focus this shaped e-beam onto the target.

An x-ray beam is then emitted from the portion of the target on which the shaped e-beam is incident. This source spot on the target has substantially the same proportions as the shaped e-beam, and generates an x-ray beam that can be focused back down to an illuminated spot at a remote location having the same non-unitary aspect ratio as the shaped e-beam. Because the entire x-ray beam is generated from the "shaped" source spot, it can be focused to a much brighter illuminated spot (i.e., higher intensity) than would be possible from a "shaped" x-ray beam formed by placing an aperture in the path of the x-ray beam.

According to another embodiment of the present invention, a microfocus x-ray tube includes a target comprising a metal strip in the shape of the desired x-ray beam cross section. An incident e-beam then generates the desired x-rays only from the metal strip, resulting in a source spot having the same proportions as the metal strip. The resulting x-ray beam can therefore produce a high brightness illuminated spot at a remote location. According to one embodiment of the present invention, the metal strip can comprise a raised strip micromachined on the surface of a bulk metal substrate. A filler layer covering the rest of the machined surface would prevent x-ray generation from the bulk metal substrate. The filler layer could comprise an insulating material, or could comprise a metal other than that of the bulk metal substrate (so that any x-rays generated by the secondary layer would be of a different wavelength than those generated by the metal strip). According to another embodiment of the present invention, the metal strip can comprise a metal layer deposited on a support substrate and then etched to the desired shape. Once again, the support substrate can be an insulating material or a metal other than that used to form the metal strip.

A x-ray reflectometry system in accordance with another embodiment of the present invention comprises a microfocus x-ray tube for producing an x-ray beam, an x-ray reflector for focusing the x-ray beam onto a test sample, a stage for holding the test sample, and an angle-limiting gate. The angle-limiting gate is opaque to the x-rays in the x-ray beam, and blocks the x-rays in the x-ray beam that fall within a certain range of relative angles (with the surface of the test sample). Therefore, the x-rays that do reach the surface of the test sample still include multiple incident angles, but simply span a reduced range. The angle-limiting gate can be placed between the microfocus x-ray tube and the reflector, or between the reflector and the test sample. According to an embodiment of the present invention, the x-ray beam comprises an elongated cross section, with the long dimension of the x-ray beam being aligned with the neutral axis of the x-ray reflectometry system.

According to an embodiment of the present invention, the angle-limiting gate can be positioned to block the x-rays having incident angles less than a specified threshold angle. X-rays having shallow incident angles have a greater likelihood of scattering and are therefore more likely to corrupt the measured signal. Therefore, by blocking those low-angle x-rays, a more accurate measurement can be made of the reflectivity curve for the high-angle x-rays. According to an embodiment of the present invention, the angle-limiting gate can then be positioned to block the x-rays having incident angles greater than the specified threshold angle, so that the reflectivity curve for the low-angle x-rays can be measured. The two halves of the reflectivity curve can then be combined to generate the final reflectivity curve.

According to an embodiment of the present invention, a secondary guard gate can be placed after the angle-limiting gate. Any x-ray scattering from the edge of the angle-limiting gate would then be blocked by the secondary guard gate. By positioning the secondary guard gate slightly below the specified critical angle, the scattered x-rays can be captured without interfering with the portion of the original x-ray beam passed by the angle-limiting gate.

According to another embodiment of the present invention, two angle-limiting gates can be used. The first angle-limiting gate can be positioned to block x-rays having incident angles less than a lower threshold angle, while the second angle-limiting gate could block x-rays having incident angles greater than an upper threshold angle. The reflectivity curve could then be generated in segments by shifting the positions of the two angle-limiting gates over the range of incident angles within the x-ray beam. The two angle-limiting gates could be replaced by a single angle-limiting gate having an aperture, the aperture being sized to pass only those x-rays within a certain range of incident angles.

The present invention will be more fully understood in view of the following description and drawings.

BRIEF DESCRIPTION OF THE DRAWINGS

FIG. 2 shows an example of a reflectivity curve.

DETAILED DESCRIPTION

Figure 5A:
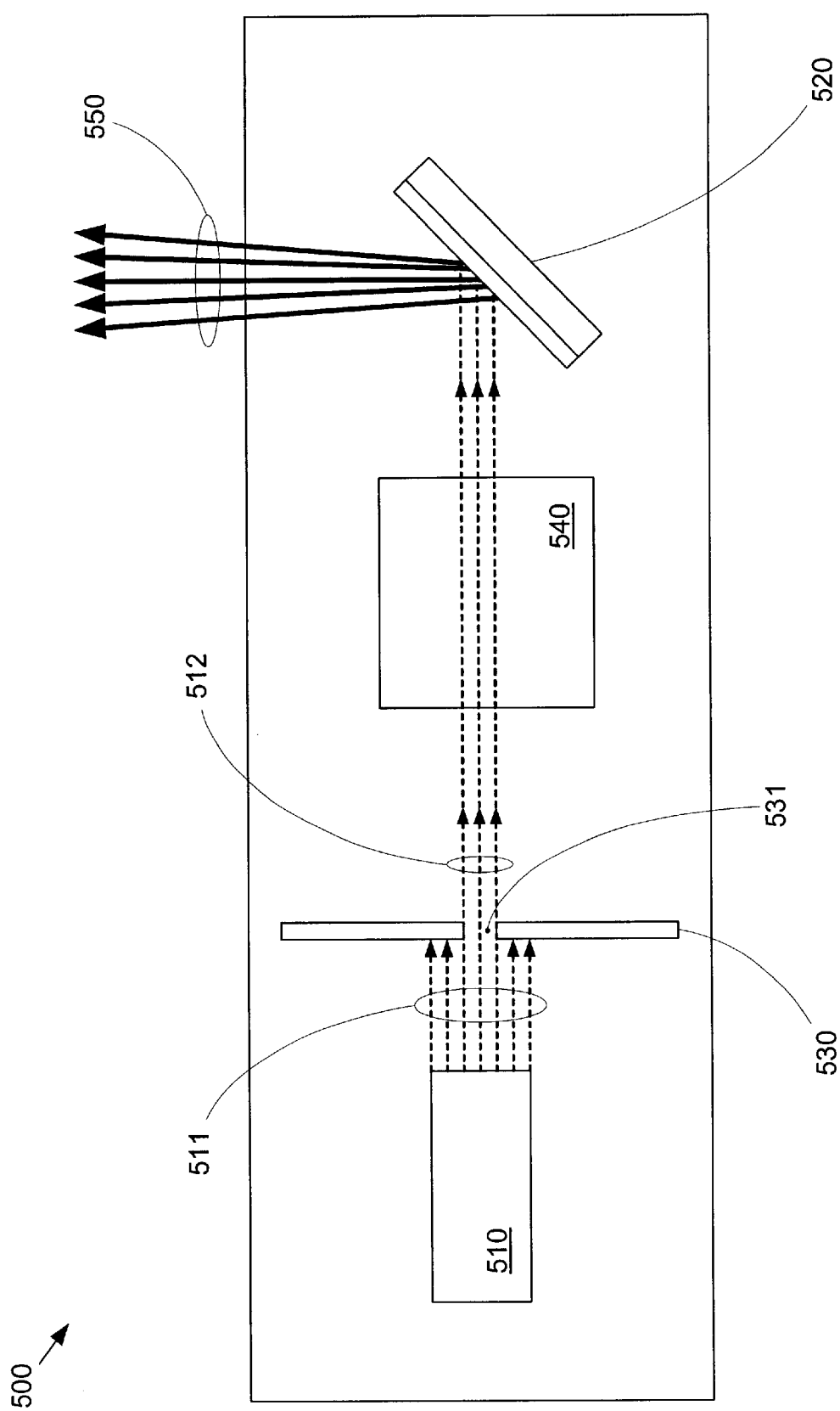
FIG. 5a shows a microfocus x-ray tube in accordance with an embodiment of the present invention.
Figure 5B:
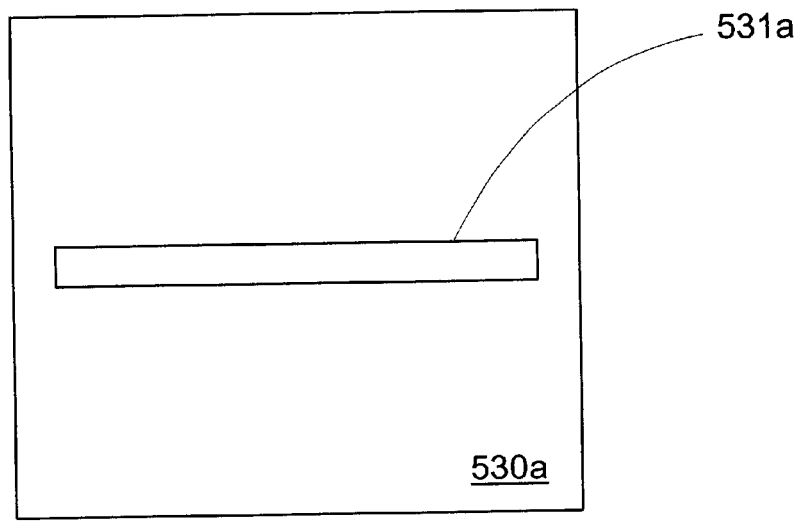
FIGS. 5b and 5c show e-beam shaping elements in accordance with embodiments of the present invention.
Figure 5C:
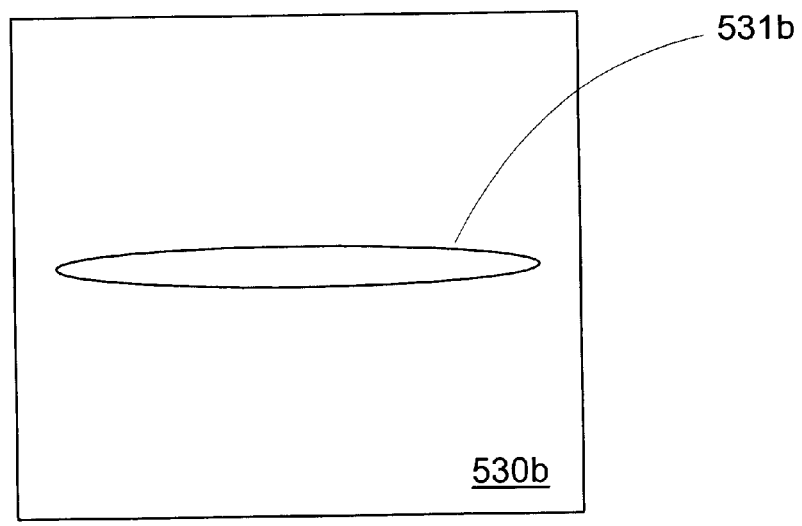

An embodiment of the present invention provides a system for producing a reduced-size x-ray beam, thereby enabling higher resolution measurement of thin films in an x-ray reflectometry system. FIG. 5a shows a microfocus x-ray tube 500 in accordance with an embodiment of the present invention. Microfocus x-ray tube 500 comprises an electron source 510, a target 520, an electron beam (e-beam) shaping element 530, and an optional electron focusing optics system 540. Electron source 510 generates a source e-beam 511 that is directed at target 520. E-beam shaping element 530, positioned between electron source 510 and target 520, is substantially opaque to source e-beam 511. An e-beam aperture 531 in e-beam shaping element 530 transmits a portion of source e-beam 511 as a shaped e-beam 512 having a non-unitary aspect ratio. According to an embodiment of the present invention, e-beam aperture 531 comprises a narrow slit that restricts shaped e-beam 512 to a very thin cross section. An example e-beam shaping element 530a having a rectangular e-beam aperture 531a is shown in FIG. 5b. Another example e-beam shaping element 530b having an oval e-beam aperture 531b is shown in FIG. 5c. Other e-beam aperture configurations will be apparent to one of ordinary skill in the art.

Returning to FIG. 5a, shaped e-beam 512 is directed towards target 520. Note that because e-beam aperture 531 has a non-unitary aspect ratio, it has a long dimension and a short dimension. To ensure that x-ray beam 550 can be focused back to these proportions at the surface of the film being measured, the long dimension of beam aperture 531 should be parallel to the surface of target 520 and perpendicular to the beam direction of x-ray beam 550. Optional electron focusing optics system 540 can be included in microfocus x-ray tube 500 to enhance the sharpness of shaped e-beam 512 as it strikes target 520. Electron focusing optics system 540 can incorporate various electron focusing techniques, including magnetic or electrostatic focusing. X-ray beam 550 is therefore emitted from a very narrow "source spot" on the target, and therefore can be focused to a narrow spot with high brightness at a location remote from microfocus x-ray tube 500 (e.g., at the surface of the film being measured)

Figure 6:
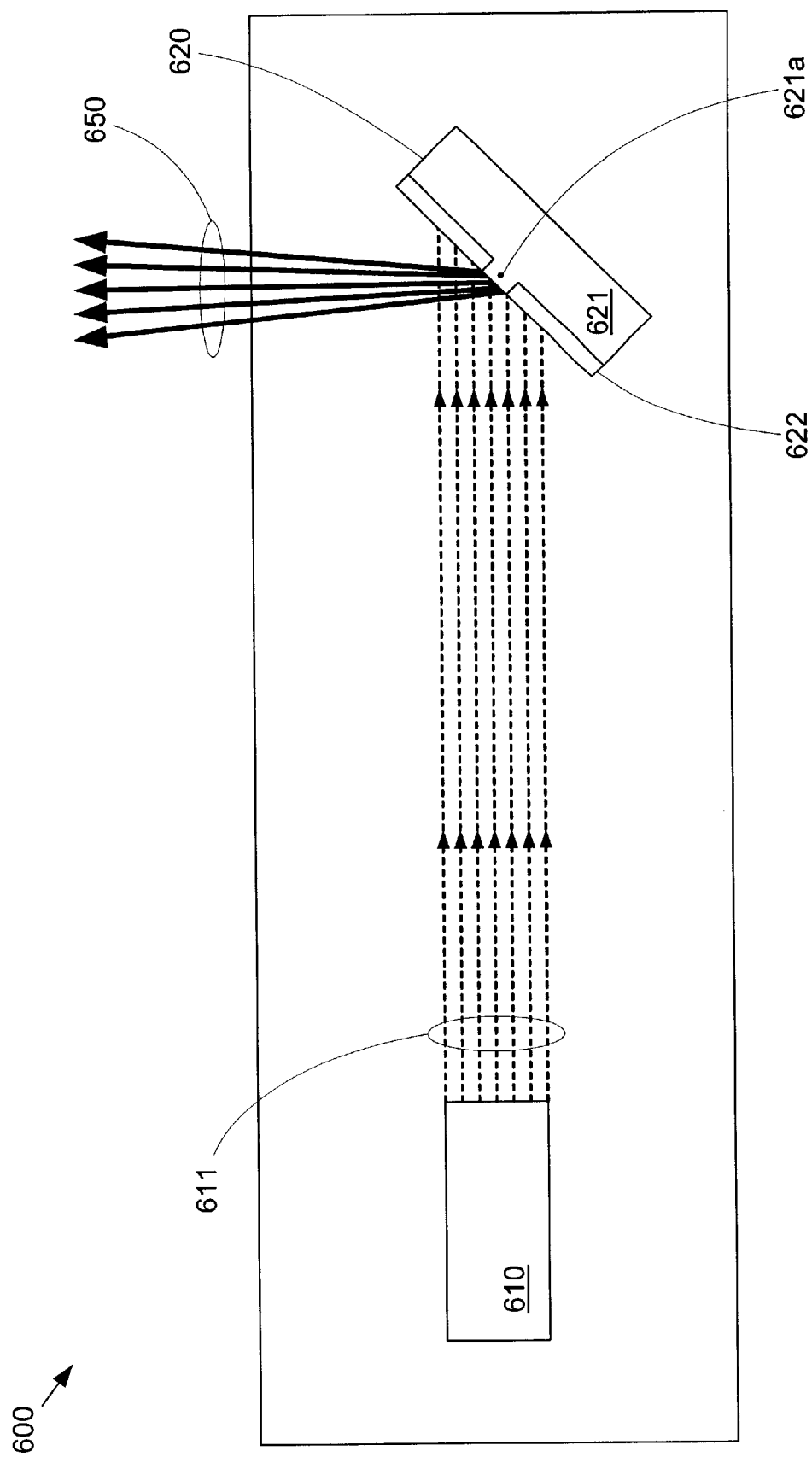
FIG. 6 shows a microfocus x-ray tube in accordance with another embodiment of the present invention.

FIG. 6 shows a microfocus x-ray tube 600 in accordance with another embodiment of the present invention. Microfocus x-ray tube 600 comprises an electron source 610 and a target 620. Electron source 610 generates a source e-beam 611 that is directed at target 620. Target 620 comprises a bulk metal base 621, on which a target strip 621a having a non-unitary aspect ratio (plan view) has been micromachined. According to an embodiment of the present invention, target strip 621a comprises a narrow strip having a rectangular or oval plan view. Target strip 621a is surrounded by a target filler layer 622, such that only the top surface of target strip 621a is showing. When source e-beam 611 strikes target 620, target strip 621a is the only portion that emits the x-rays that form x-ray beam 600, and therefore defines the source spot for x-ray beam 600. Like x-ray beam 500 shown in FIG. 5, because x-ray beam 650 is emitted from a very narrow source spot on the target, it can be focused to a narrow spot with high brightness at a location remote from microfocus x-ray tube 600.

Bulk metal base 621 comprises a metal (e.g., tungsten, molybdenum, copper) selected to generate the desired x-rays when exposed to source e-beam 611. Unwanted x-ray generation from the areas surrounding target strip 621a is prevented by target filler layer 622. According to an embodiment of the present invention, target filler layer 622 comprises an insulating material (e.g., diamond, silicon carbide, silicon) that does not transmit source e-beam 611 to the covered portion of bulk metal base 621. According to another embodiment of the present invention, target filler layer 622 comprises a metal different than that used in the bulk metal base 621. Even though target filler layer 622 might then generate x-rays when exposed to source e-beam 611, those x-rays would be of a different wavelength than the x-rays generated by target strip 621a, and therefore could be readily filtered away by a monochromator. In either case, the desired x-rays are only emitted by target strip 621a.

Figure 7:
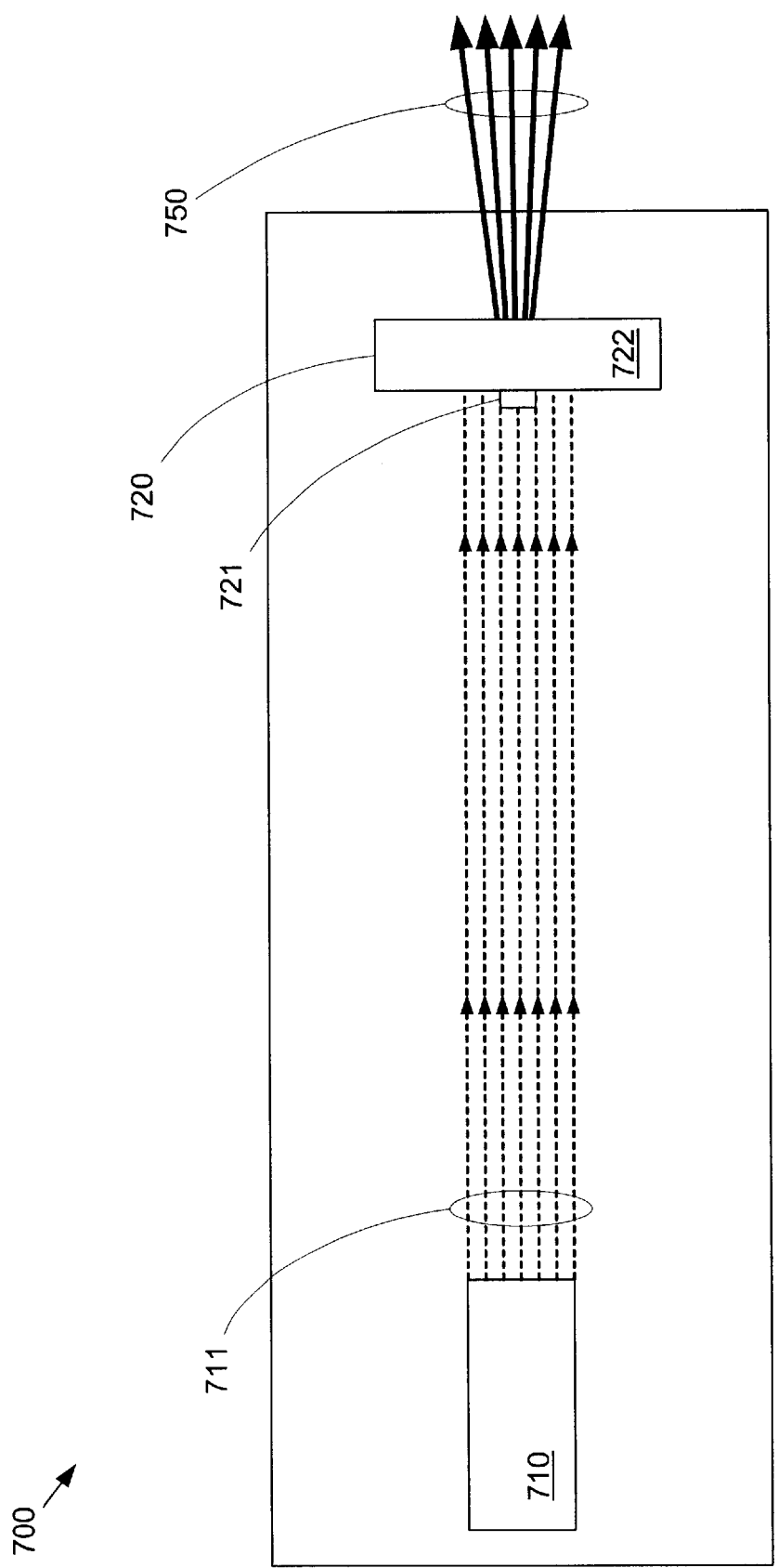
FIG. 7 shows a microfocus x-ray tube in accordance with another embodiment of the present invention.

FIG. 7 shows a microfocus x-ray tube 700 in accordance with another embodiment of the present invention. Microfocus x-ray tube 700 comprises an electron source 710 and a target 720. Electron source 710 generates a source e-beam 711 that is directed at target 720. Target 720 comprises a metal target strip 721 formed on a target substrate 722. According to an embodiment of the present invention, metal target strip 721 comprises a narrow strip of metal having a rectangular or oval plan view. When source e-beam 711 strikes target 720, metal target strip 721 defines the source spot that emits x-ray beam 750.

According to an embodiment of the present invention, target strip 721 can be formed by depositing a layer of metal on target substrate 722 and then etching away the unwanted portions of the layer. Metal target strip 721 can comprise tungsten, molybdenum, copper, or any other metal selected to provide the desired x-rays under source e-beam 711. According to an embodiment of the present invention, target substrate 722 comprises an insulating material (e.g., diamond, silicon carbide, silicon). According to another embodiment of the present invention, target 722 comprises a metal different than that used in metal target strip 721. In either case, only metal target strip 721 emits the desired x-rays when target 720 is exposed to source e-beam 711.

Figure 1A:
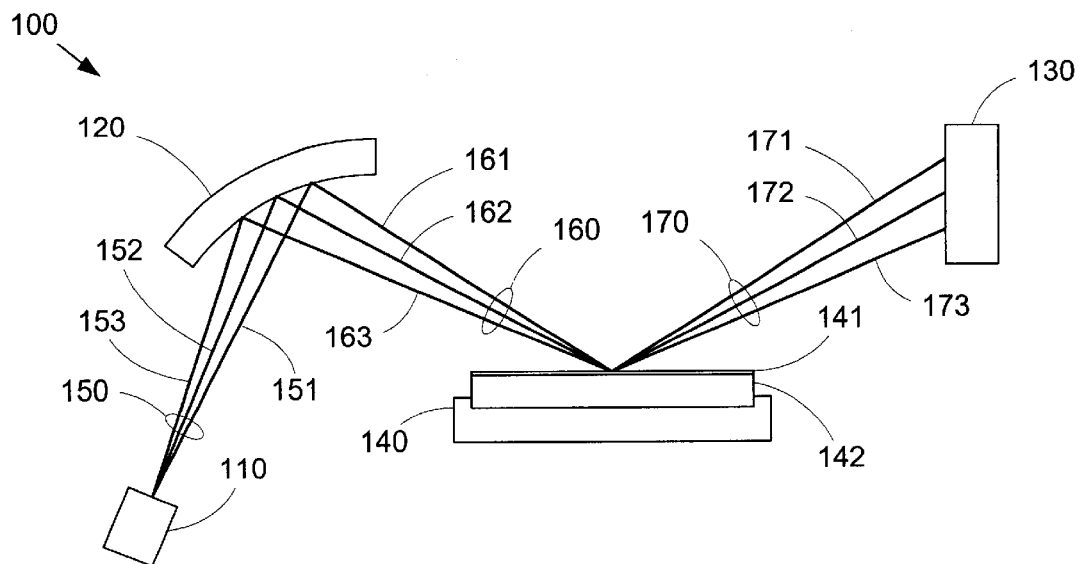
FIG. 1a shows a conventional x-ray reflectometry system.
Figure 1B:
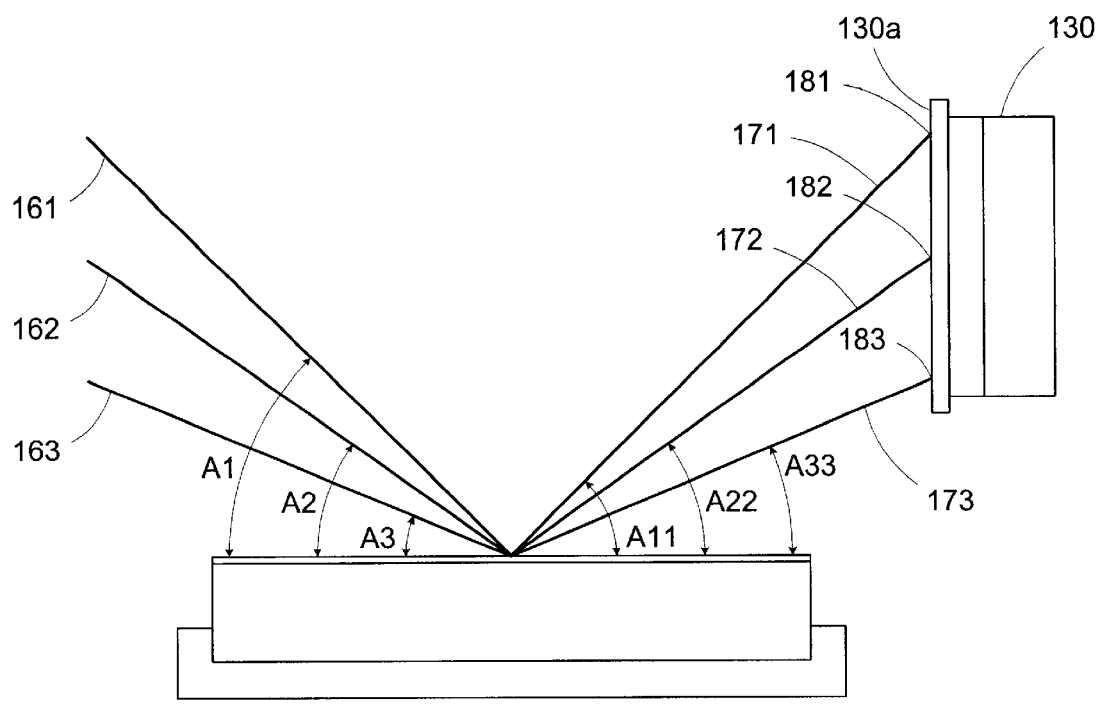
FIG. 1b shows a detail view of x-ray reflections onto a detector in a conventional x-ray reflectometry system.
Figure 1C:
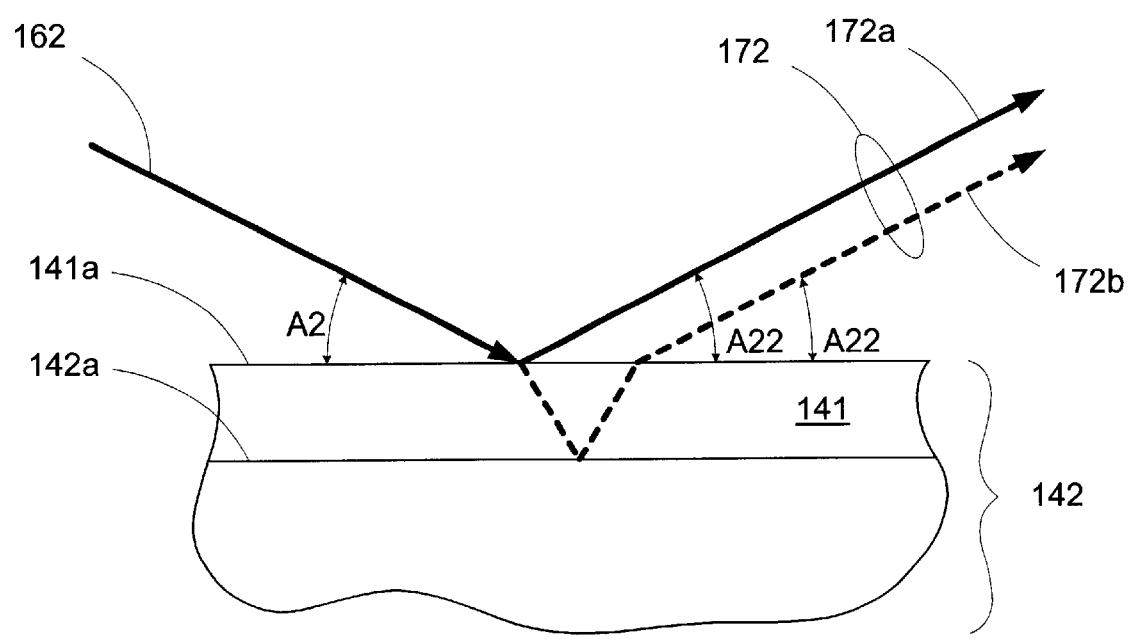
FIG. 1c shows a detail view of x-ray beam reflection at the surface of a thin film layer.
Figure 3:
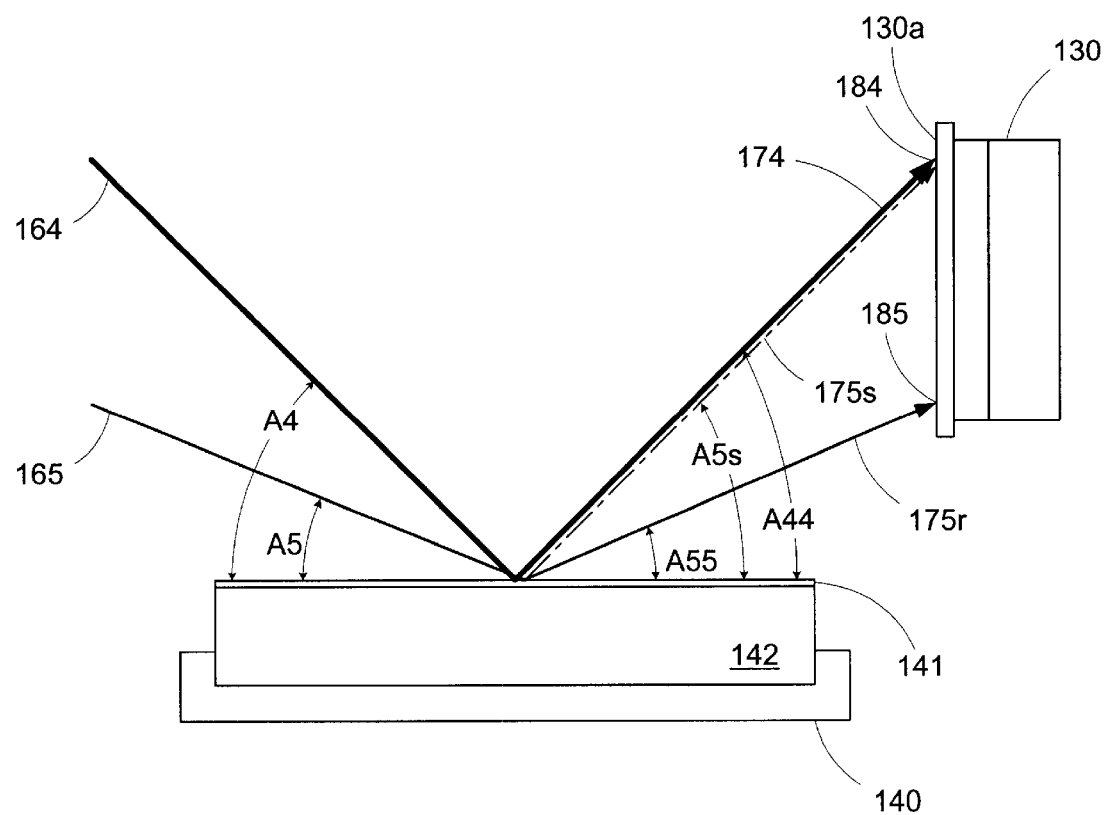
FIG. 3 shows an example of scattering in an x-ray reflectometry system.
Figure 4A:
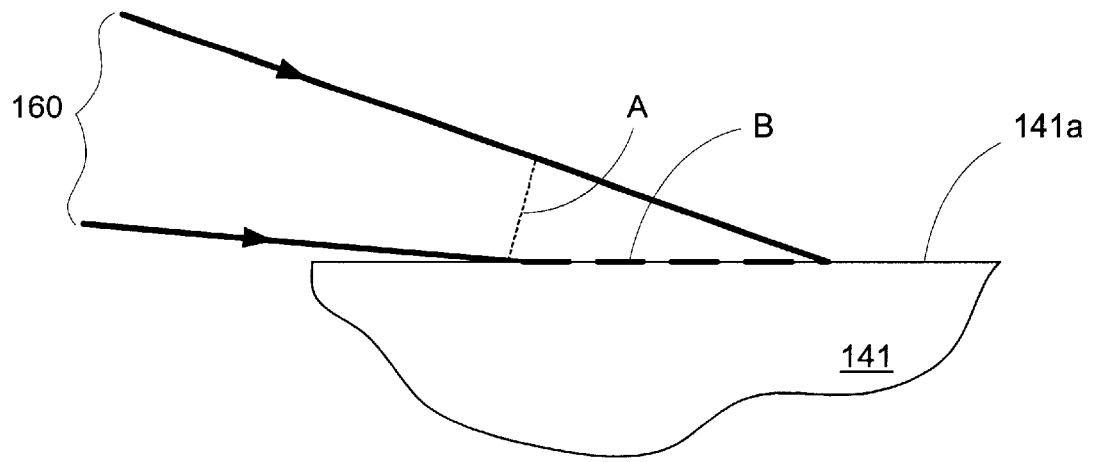
FIGS. 4a and 4b show details of x-ray beam spreading in a conventional x-ray reflectometry system.
Figure 4B:
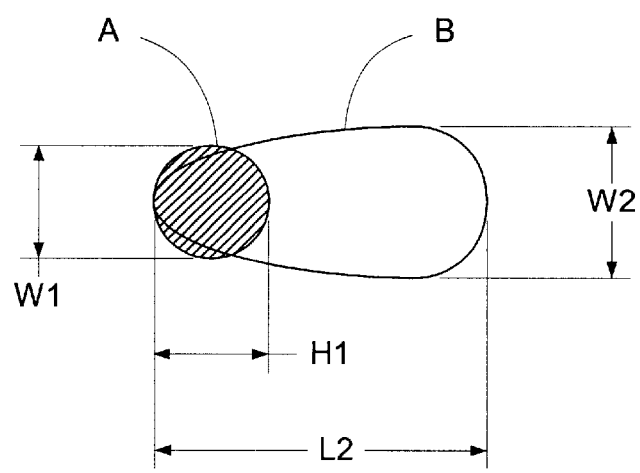
Figure 8A:
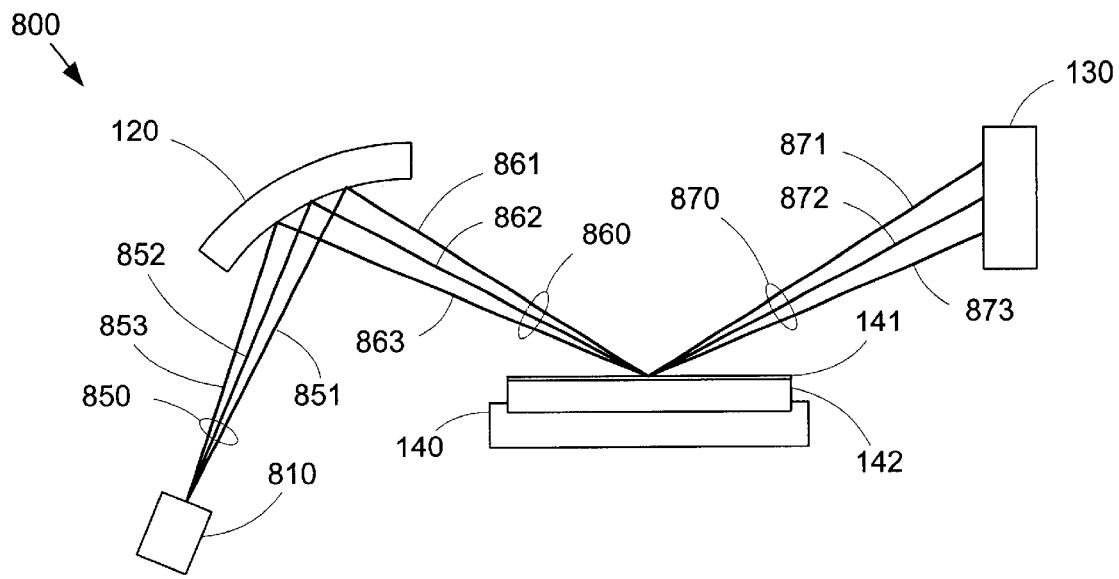
FIG. 8a shows an x-ray reflectometry system providing reduced illuminated spot size, in accordance with an embodiment of the present invention.

FIG. 8a shows an x-ray reflectometry system 800 in accordance with an embodiment of the present invention. X-ray reflectometry system 800 is substantially similar to x-ray reflectometry system 100 shown in FIG. 1a, except conventional microfocus x-ray tube 110, which uses a circular source spot, is replaced with microfocus x-ray tube 810, which generates an x-ray beam 850 from a source spot having a non-unitary aspect ratio. According to an embodiment of the present invention, microfocus x-ray tube 810 comprises an electron beam shaping element between an electron beam source and a target, as described with respect to microfocus x-ray tube 500 shown in FIG. 5a. According to another embodiment of the present invention, microfocus x-ray tube 810 includes a target comprising a narrow strip micromachined from a metal base and surrounded by a filler layer, as described with respect to microfocus x-ray tube 600 shown in FIG. 6. According to another embodiment of the present invention, microfocus x-ray tube includes a target comprising a thin metal strip formed on a substrate, as described with respect to microfocus x-ray tube 700 shown in FIG. 7.

X-ray reflectometry system 800 operates in a manner substantially similar to that previously described with respect to x-ray reflectometry system 100. Source x-ray beam 850 is reflected and focused by x-ray reflector 120 as converging x-ray beam 860 onto thin film layer 141, and output x-ray beam 870 is measured and spatially resolved by detector 130 to generate a reflectivity curve for thin film layer 141.

Figure 8B:
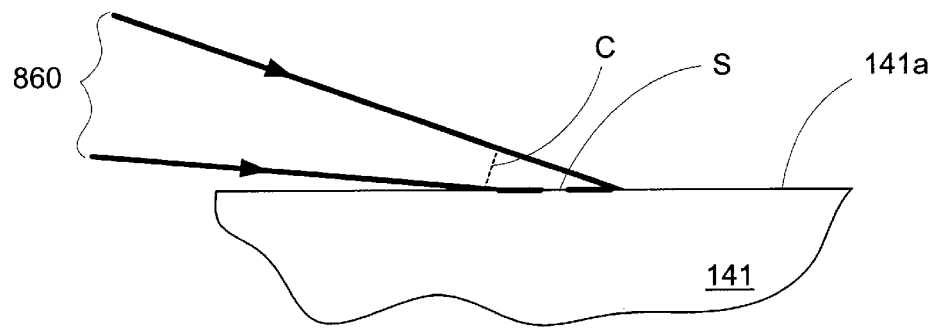
FIGS. 8b and 8c show details of x-ray beam spreading in an x-ray reflectometry system in accordance with an embodiment of the present invention.

Microfocus x-ray tube 810 is oriented such that the long dimension of the source spot generating x-ray beam 860 is aligned with the neutral axis of x-ray reflectometry system 800 (i.e., perpendicular to the beam direction of x-ray beam 860 and parallel to the plane of thin film surface 141a). A detail view of x-ray beam 860 striking thin film layer 141 is shown in FIG. 8b. X-ray beam 860 is focused to a minimum x-ray beam cross section C, and forms an illuminated spot S where thin film surface 141a intersects x-ray beam 860. As with conventional x-ray reflectometry systems, the area of illuminated spot S is greater than cross section C due to spreading at thin film surface 141a. However, the length (in the beam direction) of illuminated spot S is minimized by the narrow height of x-ray beam cross section C.

Figure 8C:
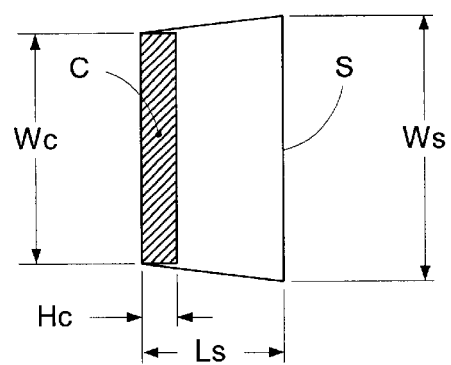

For example, FIG. 8c shows cross section C overlaid on illuminated spot S, according to an embodiment of the present invention. Cross section C has a height Hc and a width Wc, where width Wc is significantly greater than height Hc. Although shown as having a substantially rectangular outline, cross section C could have any outline with a non-unitary aspect ratio. Illuminated spot S has a length Ls and a width Ws at its largest dimensions. As expected, while width Ws exhibits only a slight increase from x-ray beam cross sectional width Wc, the length Ls of illuminated spot S in the beam direction is much greater than x-ray beam cross sectional height Hc.

Despite this unavoidable elongation, the actual length Ls of illuminated spot S is still greatly reduced compared to conventional x-ray reflectometry systems. Height Hc of x-ray beam 860 is substantially smaller than the cross sectional height of x-ray beams in conventional x-ray reflectometry systems. Therefore, length Ls of illuminated spot S is also significantly smaller than the length of the illuminated spot in those conventional x-ray reflectometry systems.

For example, the minimum (circular) source spot diameter of a conventional microfocus x-ray tube is limited to about 25 microns to prevent overheating of the target. At a 0.5 degree incident angle, the illuminated spot produced by such a microfocus x-ray tube will stretch out to roughly 3.5 mm. In contrast, a microfocus x-ray tube in accordance with the present invention can produce similar x-ray output from a 1 micron by 25 micron rectangular source spot, due to the enhanced heat conduction capability provided by the high perimeter to area ratio of the source spot. The resulting narrow illuminated spot will thus only stretch to about 115 microns on the thin film surface, thereby providing an order of magnitude higher resolution over the conventional microfocus x-ray tube.

Figure 9A:
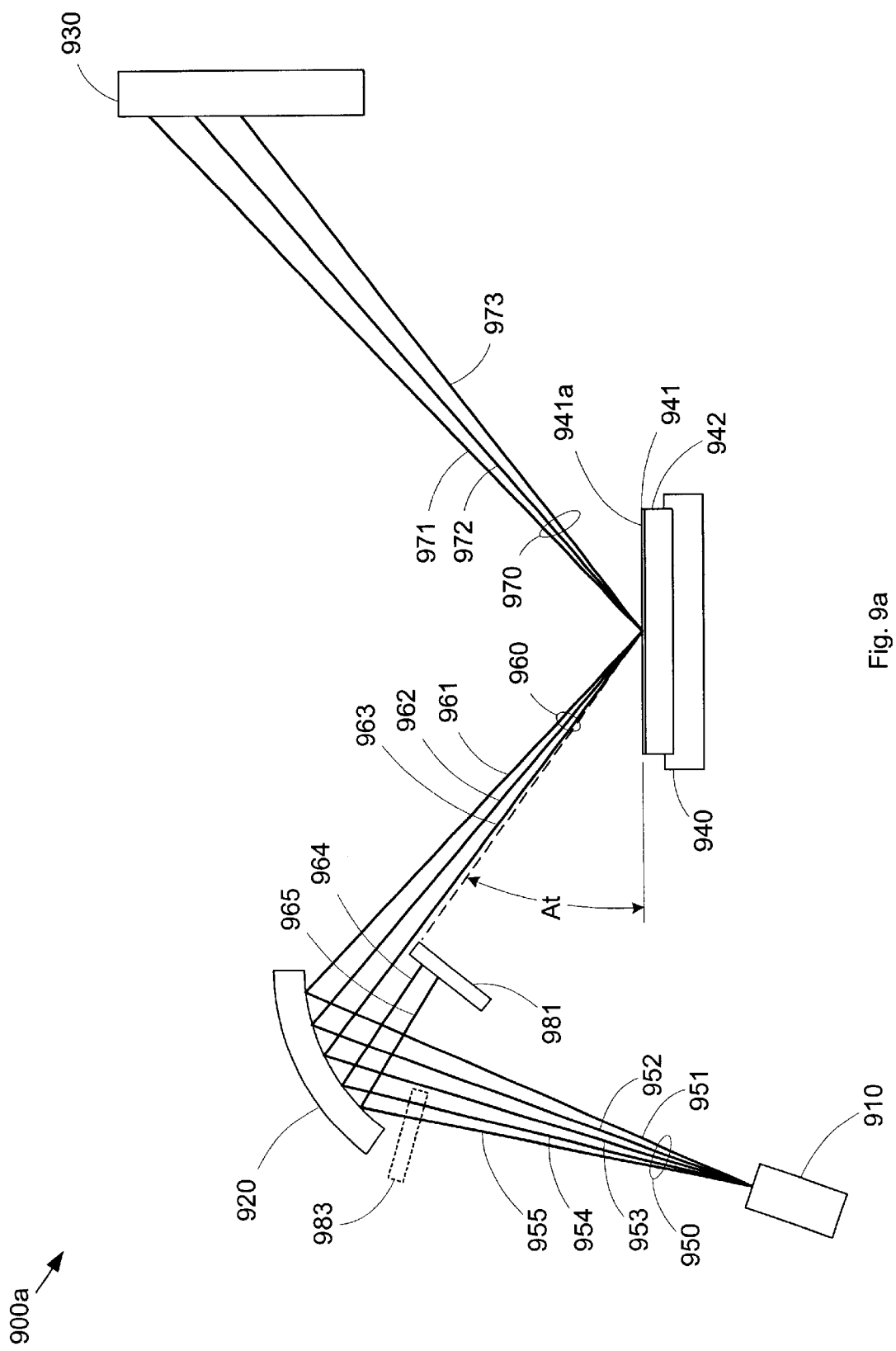
FIGS. 9a–9d show various x-ray reflectometry systems for minimizing the effects of scattering, according to various embodiments of the present invention.

FIG. 9a shows an x-ray reflectometry system 900a in accordance with another embodiment of the present invention. X-ray reflectometry system 900a comprises a microfocus x-ray tube 910, an x-ray reflector 920, a detector 930, a stage 940, and an angle-limiting gate 981. Microfocus x-ray tube 910 is configured to generate a source x-ray beam 950. X-ray reflector 920 reflects and focuses source x-ray beam 950 into a converging x-ray beam 960 directed at a thin film layer 941 on a test sample 942. Test sample 942 is held in place by stage 940. Converging x-ray beam 960 is then reflected by thin film layer 941 onto detector 930 as an output x-ray beam 970. According to an embodiment of the present invention, x-ray reflector 920 comprises a monochromator. According to another embodiment of the present invention, microfocus x-ray tube 910 generates an x-ray beam from a source spot having a non-unitary aspect ratio, the long dimension of the source spot being aligned with the neutral axis of x-ray reflectometry system 900a.

Angle limiting gate 981 is opaque to x-rays and can be positioned to prevent a portion of the x-rays emitted by microfocus x-ray tube 910 from reaching thin film layer 941. According to an embodiment of the present invention, angle-limiting gate 981 is configured to block only those x-rays in x-ray beam 960 forming a relative angle with thin film surface 941a less than a threshold angle At. For example, source x-ray beam 950 includes individual x-rays 951–955, which correspond to x-rays 961–965, respectively, in focused x-ray beam 960. X-rays 961–963, which form relative angles with thin film surface 941a that are greater than threshold angle At, are not affected by angle limiting gate 981 and are reflected as x-rays 971–973, respectively, in output x-ray beam 970. However, x-rays 964 and 965, which form relative angles with thin film surface 941a that are less than threshold angle At, are blocked by angle limiting gate 981. Therefore, x-rays 964 and 965 never reach thin film layer 941 and so cannot scatter to contaminate the measurements of x-rays 971–973 by sensor 930.

According to another embodiment of the present invention, angle-limiting gate could be replaced by an angle-limiting gate 983 (indicated by a dotted outline). Rather then being positioned between x-ray reflector 920 and stage 940, angle-limiting gate 983 could be placed between microfocus x-ray tube 910 and x-ray reflector 920. Angle-limiting gate 983 would then block those x-rays in source x-ray beam 950 corresponding to those x-rays in focused x-ray beam 960 forming a relative angle with thin film surface 941 less than threshold angle At.

Figure 9B:
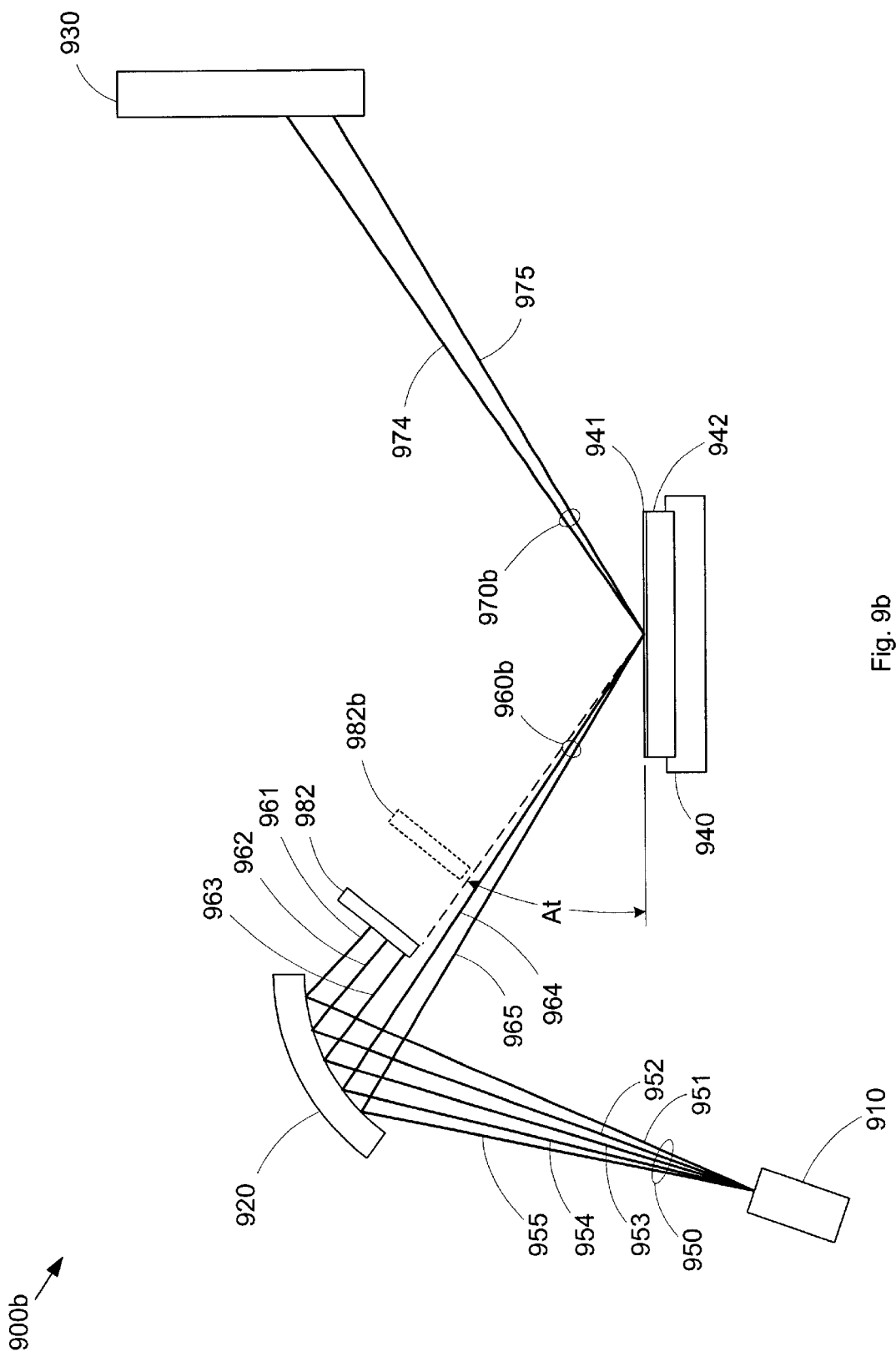

FIG. 9b shows an x-ray reflectometry system 900b in accordance with another embodiment of the present invention. X-ray reflectometry system 900b is substantially similar to x-ray reflectometry system 900a shown in FIG. 9a, except that angle limiting gate 981 is replaced with an angle limiting gate 982. Rather than blocking x-rays below threshold angle At, angle limiting gate 982 blocks those x-rays forming relative angles with thin film surface 941 greater than threshold angle At. Therefore, x-rays 964 and 965 are passed by angle-limiting gate 981 and are reflected as x-rays 974 and 975, respectively, while x-rays 964 and 965, which form relative angles with thin film surface 941a that are less than threshold angle At, are blocked. Therefore, measurements of x-rays 974 and 975 by sensor 930 are not contaminated by scattering from x-rays 961–963.

According to an embodiment of the present invention, x-ray reflectometry system 900a shown in FIG. 9a could be used in conjunction with x-ray reflectometry system 900b, thereby facilitating measurement across the full range of x-rays in source x-ray beam 950. A measurement with only angle-limiting gate 981 in place could be performed, followed by a measurement with only angle-limiting gate 982 in place. The results of the two measurements could be combined to obtain the complete reflectivity curve. According to another embodiment of the present invention, angle-limiting gates 981 and 982 shown in FIGS. 900a and 900b, respectively, could represent two positions of a single movable angle-limiting gate.

According to another embodiment of the present invention, angle-limiting gate 982 of x-ray reflectometry system 900b could be removable, in which case two measurements could be taken—one with angle-limiting gate 982 in place, and one with angle-limiting gate 982 removed. Scattering effects detected in the gated first measurement could then be subtracted from the results of the non-gated measurement. X-ray reflectometry system 900a could be operated in a similar manner.

Figure 9C:
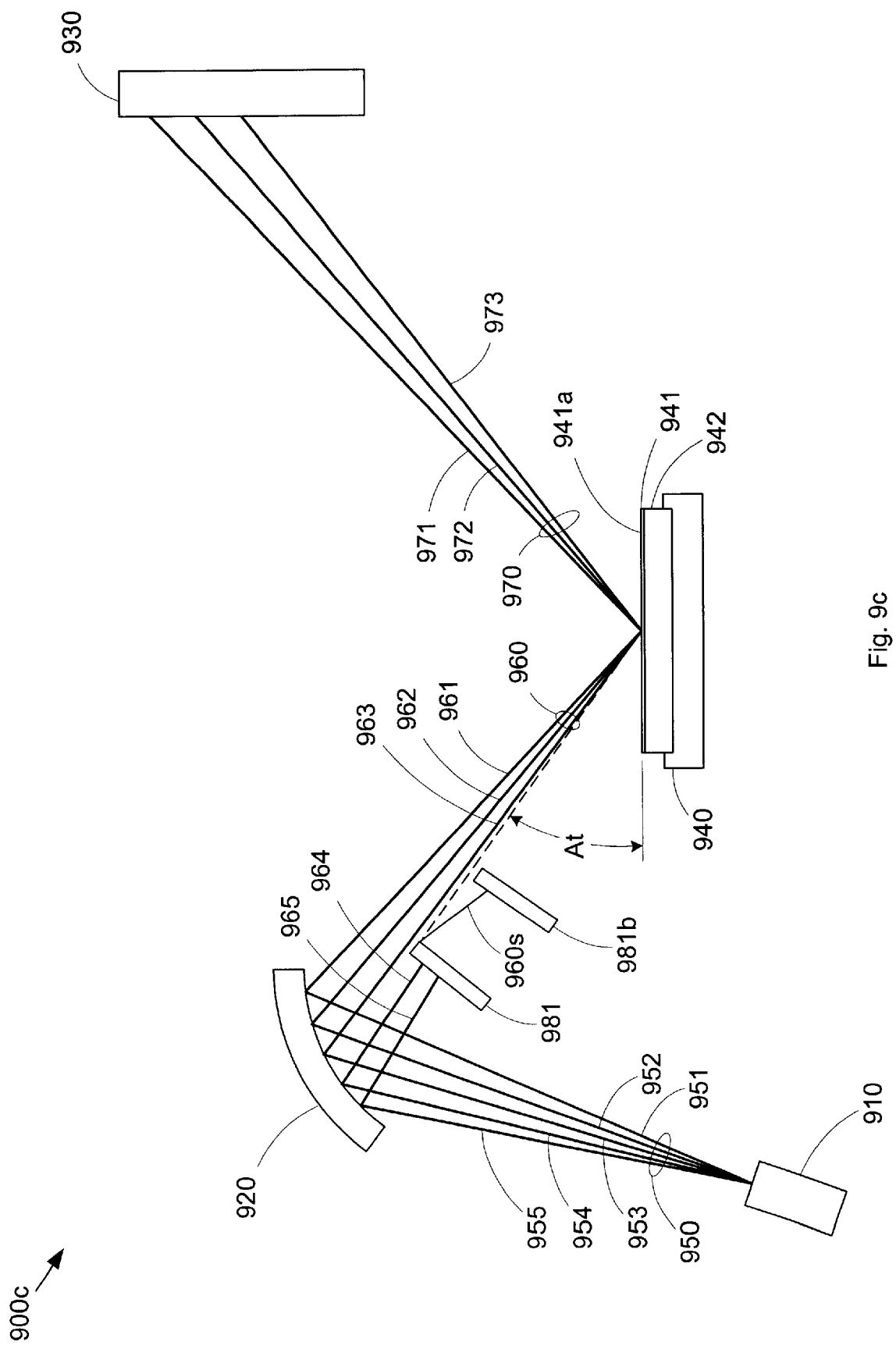

FIG. 9c shows an x-ray reflectometry system 900c in accordance with another embodiment of the present invention. X-ray reflectometry system 900c includes a secondary guard gate 981b between angle limiting gate 981 and test sample 942. In other respects, x-ray reflectometry system 900c is substantially similar to x-ray reflectometry system 900a shown in FIG. 9a. Secondary guard gate 981b is aligned in the beam direction with angle limiting gate 981, but positioned slightly below the beam horizon, i.e., the edge of secondary guard gate 981b is positioned so as to be just below the x-rays passed by angle-limiting gate 981. Therefore, secondary guard gate does not affect the x-rays above threshold angle At, but can block any x-rays scattered from the edge of angle-limiting gate 981, such as x-ray 960s. In this manner, secondary guard gate further enhances the accuracy of the measurements taken by detector 930. A similar secondary guard gate 982b (indicated by a dotted outline) could be added to x-ray reflectometry system 900b shown in FIG. 9b, to block scattering from the edge of angle-limiting gate 982.

Figure 9D:
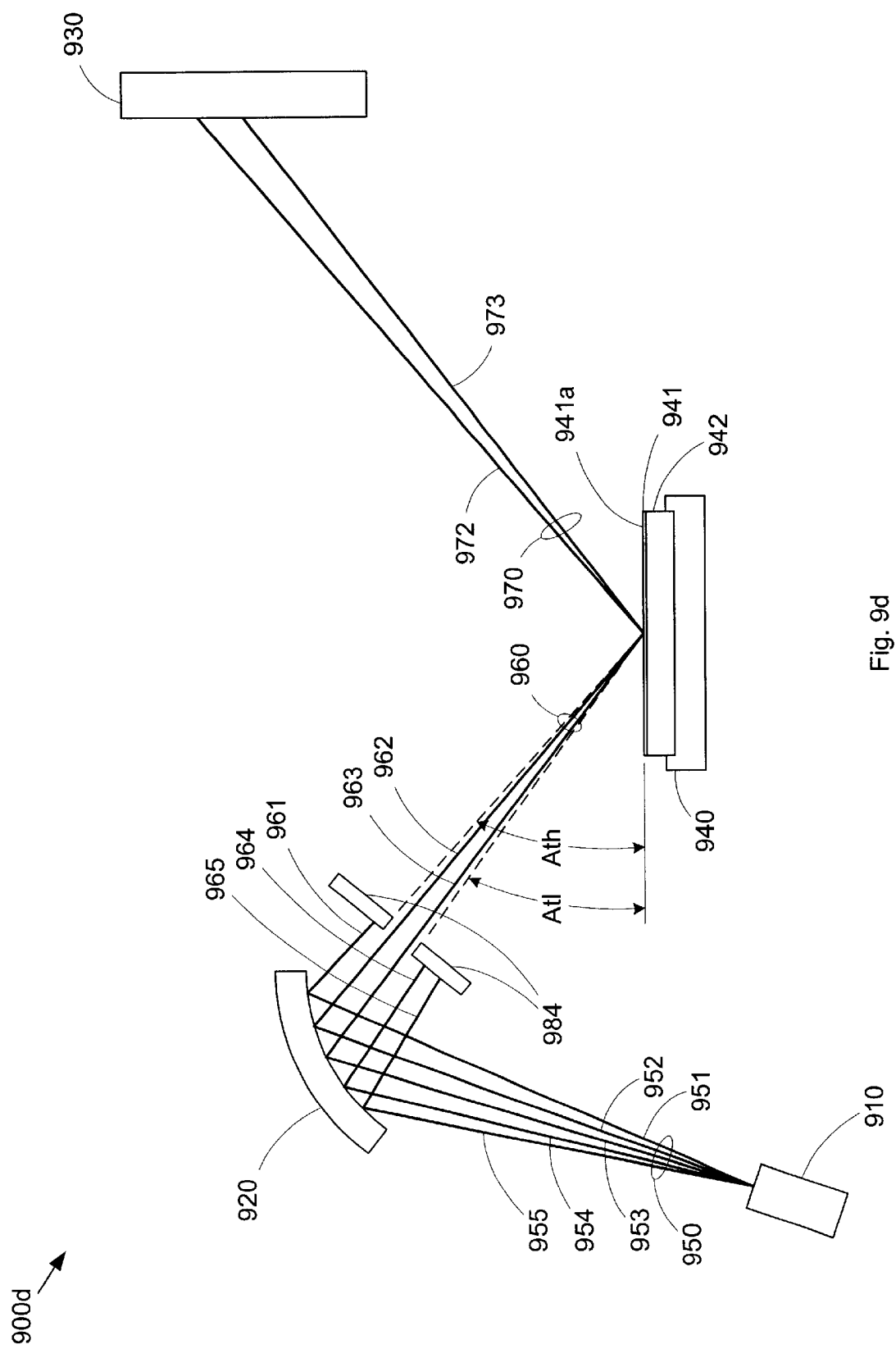

FIG. 9d shows an x-ray reflectometry system 900d in accordance with another embodiment of the present invention. X-ray reflectometry 900d is substantially similar to x-ray reflectometry system 900a shown in FIG. 9a, except that angle-limiting gate 981 of x-ray reflectometry system 900a is replaced with a slotted gate 984 in x-ray reflectometry system 900d. Only those x-rays forming relative angles with thin film surface 941a between a lower threshold angle Atl and an upper threshold angle Ath are passed by slotted gate 984 to thin film layer 941. By adjusting the position of slotted gate 984 with respect to x-ray reflector 920, a series of reflectivity measurements can be taken. The individual measurements can then be combined to form a complete reflectivity curve.

Although the present invention has been described in connection with several embodiments, it is understood that this invention is not limited to the embodiments disclosed, but is capable of various modifications that would be apparent to one of ordinary skill in the art. Thus, the invention is limited only by the following claims.

I claim:

1. An x-ray reflectometry system for measuring the thickness of a thin film layer on a test sample, the x-ray reflectometry system comprising:

an x-ray tube for generating an x-ray beam comprising a plurality of x-rays;

a stage for supporting the test sample to position a top surface of the thin film location at a measurement location;

an x-ray reflector for focusing the x-ray beam at a the measurement location;

a first gate for blocking a first group of the plurality of x-rays without impeding a second group of the plurality of x-rays, the second group of the plurality of x-rays forming a plurality of incident angles with the measurement location; and a second gate for blocking x-rays scattered by the first gate without impeding the second group of the plurality of x-rays.

2. The x-ray reflectometry system of claim 1, wherein the x-ray reflector comprises a monochromator.

3. The x-ray reflectometry system of claim 1, wherein each the second group of the plurality of x-rays forms a relative angle with the measurement location less than a threshold angle.

4. The x-ray reflectometry system of claim 1, wherein each of the second group of the plurality of x-rays forms a relative angle with the measurement location greater than a threshold angle.

5. The x-ray reflectometry system of claim 1, the first gate being positioned between the x-ray reflector and the stage.

6. The x-ray reflectometry system of claim 1, the first gate being positioned between the x-ray tube and the x-ray reflector.

7. The x-ray reflectometry system of claim 1, wherein the first gate comprises an aperture.

8. An x-ray reflectometry system for measuring the thickness of a thin film layer on a test sample, the x-ray reflectometry system comprising:
   means for producing a first x-ray beam from a source spot having proportions having a non-unitary aspect ratio, the means for producing the first x-ray beam including a beam shaping element having proportions substantially similar to the proportions of the source spot;
   means for focusing the first x-ray beam onto the thin film layer; and
   means for measuring a second x-ray beam reflected by the thin film layer.

9. The x-ray reflectometry system of claim 8, wherein the means for producing the first x-ray beam further comprises:
   a target; and
   an electron source, the electron source being configured to generate an electron beam, the target being configured to emit the first x-ray beam in response to the electron beam;
   wherein the beam shaping element comprises an aperture between the electron source and the target, the aperture having proportions substantially equal to the proportions of the source spot.

10. The x-ray reflectometry system of claim 8, wherein the means for producing the first x-ray beam further includes a target comprising:
    a bulk metal base having a top surface, wherein the beam shaping element comprises a micromachined strip being formed on the top surface, wherein plan view proportions of the micromachined strip are substantially equal to the proportions of the source spot; and
    a filler layer, the filler layer covering the top surface of the bulk metal base around the micromachined strip.

11. The x-ray reflectometry system of claim 8, wherein the means for producing the first x-ray beam further includes a target comprising:
    a substrate;
    wherein the beam shaping element comprises a metal strip formed on the substrate, the plan view proportions of the metal strip being substantially equal to the proportions of the source spot.

12. The x-ray reflectometry system of claim 8, wherein the long dimension of the source spot is at least five times the short dimension of the metal strip.

13. The x-ray reflectometry system of claim 12, wherein the short dimension of the source spot is no greater than 20 $\mu$m.

14. An x-ray reflectometry system for measuring the thickness of a thin film layer on a test sample, the x-ray reflectometry system comprising:
    an x-ray tube for generating an x-ray beam comprising a plurality of x-rays, the x-ray beam being emitted from a source spot having a non-unitary aspect ratio;
    an x-ray reflector for focusing the x-ray beam at a top surface of the thin film layer; and
    a first gate, the first gate being substantially opaque to the x-ray beam, the first gate blocking a first group of the plurality of x-rays without impeding a second group of the plurality of x-rays, the second group of the plurality of x-rays forming a plurality of incident angles with the top surface of the thin film layer;
    wherein the x-ray tube includes a target comprising:
        a bulk metal base having a top surface, a micromachined strip being formed on the top surface, the micromachined strip having plan view proportions substantially equal to the proportions of the source spot; and
        a filler layer, the filler layer covering the top surface of the bulk metal base around the micromachined strip.

15. An x-ray reflectometry system for measuring the thickness of a thin film layer on a test sample, the x-ray reflectometry system comprising:
    an x-ray tube for generating an x-ray beam comprising a plurality of x-rays, the x-ray beam being emitted from a source spot having a non-unitary aspect ratio;
    an x-ray reflector for focusing the x-ray beam at a top surface of the thin film layer; and
    a first gate, the first gate being substantially opaque to the x-ray beam, the first gate blocking a first group of the plurality of x-rays without impeding a second group of the plurality of x-rays, the second group of the plurality of x-rays forming a plurality of incident angles with the top surface of the thin film layer,
    wherein the x-ray tube includes a target comprising:
        a substrate; and
        a metal strip formed on the substrate, the metal strip having plan view proportions substantially equal to the proportions of the source spot.

16. A method for measuring the thickness of a thin film layer on a test sample, the method comprising the steps of:
    focusing a first x-ray beam comprising a plurality of x-rays at a location on the thin film layer, wherein the plurality of x-rays form a range of relative angles with the thin film layer;
    blocking a first group of the plurality of x-rays from reaching the thin film layer;
    preventing x-rays scattered by the step of blocking the first group of the plurality of x-rays from reaching the thin film layer;
    generating a first reflectivity curve for a second x-ray beam reflected from the thin film layer;
    blocking a second group of the plurality of x-rays from reaching the thin film layer, the first group of the plurality of x-rays and the second group of the plurality of x-rays being mutually exclusive;
    generating a second reflectivity curve for a third x-ray beam reflected from the thin film layer; and
    combining the first reflectivity curve with the second reflectivity curve to form a combined reflectivity curve.

17. A method for measuring the thickness of a thin film layer on a test sample, the method comprising the steps of:
    focusing a first x-ray beam comprising a plurality of x-rays at a location on the thin film layer, wherein the plurality of x-rays form a range of relative angles with the thin film layer;

generating a first reflectivity curve by measuring a reflected x-ray beam reflected from the first x-ray beam by the thin film layer;

blocking a first group of the plurality of x-rays from reaching the thin film layer;

measuring a scattering output caused by a second group of the plurality of x-rays impinging on the thin film layer, the second group of the plurality of x-rays comprising all of the plurality of x-rays not included in the first group of the plurality of x-rays; and subtracting the scattering output from the first reflectivity curve to generate a final reflectivity curve.

18. An x-ray reflectometry system for measuring the thickness of a thin film layer of a test sample, the x-ray reflectometry system comprising:

an x-ray tube for generating an x-ray beam from a source spot having proportions having a non-unitary aspect ratio, the x-ray tube including a beam shaping element having proportions substantially similar to the proportions of the source spot; and an x-ray reflector for focusing the x-ray beam onto the thin film layer.

19. The x-ray reflectometry system of claim 18, further comprising a stage for supporting the test sample such that a top surface of the thin film layer lies in a first plane, wherein the non-unitary aspect ratio of the source spot has a long dimension and a short dimension, and wherein the x-ray beam has a beam direction, the long dimension being parallel to the first plane and perpendicular to the beam direction.

20. The x-ray reflectometry system of claim 18, wherein the x-ray tube comprises:

a target; and an electron source, the electron source being configured to generate an electron beam, the target being configured to emit the x-ray beam in response to the electron beam, wherein the beam shaping element comprises an aperture between the electron source and the target, the aperture having proportions substantially equal to the proportions of the source spot.

21. The x-ray reflectometry system of claim 20, wherein the x-ray tube further comprises an electron focusing optics system between the beam shaping element and the target.

22. The x-ray reflectometry system of claim 18, wherein the x-ray tube includes a target comprising:

a bulk metal base having a top surface, wherein the beam shaping element comprises a micromachined strip being formed on the top surface, the micromachined strip having proportions substantially equal to the proportions of the source spot; and a filler layer, the filler layer covering the top surface of the bulk metal base around the micromachined strip.

23. The x-ray reflectometry system of claim 22, wherein the filler layer comprises an insulating material.

24. The x-ray reflectometry system of claim 22, wherein the bulk metal base comprises a first metal, and wherein the filler layer comprises a second metal, the second metal being different from the first metal.

25. The x-ray reflectometry system of claim 18, wherein the x-ray tube includes a target comprising:

a substrate, wherein the beam shaping element comprises a metal strip formed on the substrate, the metal strip having proportions substantially equal to the proportions of the source spot.

26. The x-ray reflectometry system of claim 25, wherein the substrate comprises an insulating material.

27. The x-ray reflectometry system of claim 25, wherein the metal strip comprises a first metal, and wherein the substrate comprises a second metal, the second metal being different from the first metal.

28. The x-ray reflectometry system of claim 18, wherein the x-ray reflector comprises a monochromator.

29. The x-ray reflectometry system of claim 18, wherein the long dimension of the source spot is at least five times the short dimension of the source spot.

30. The x-ray reflectometry system of claim 29, wherein the short dimension of the source spot is no greater than 20 $\mu$m.

31. A method for measuring the thickness of a thin film layer formed on a test sample, the method comprising the steps of:

generating an x-ray beam from a source spot having a non-unitary aspect ratio;

aligning the long dimension of the source spot to be perpendicular to the direction of the x-ray beam and parallel to the thin film layer;

focusing the x-ray beam at a location on the thin film layer;

spatially resolving the intensity of the x-ray beam reflected by the thin film layer to generate a reflectivity curve.

* * * * *